(12) United States Patent
Chana

(10) Patent No.: US 10,191,012 B2
(45) Date of Patent: Jan. 29, 2019

(54) MONITORING ENGINE COMPONENTS

(71) Applicant: ISIS INNOVATION LIMITED, Summertown, Oxford, Oxfordshire (GB)

(72) Inventor: Kamaljit Singh Chana, Surrey (GB)

(73) Assignee: Oxford University Innovation Limited, Oxford (GB)

( * ) Notice: Subject to any disclaimer, the term of this patent is extended or adjusted under 35 U.S.C. 154(b) by 366 days.

(21) Appl. No.: 14/371,085

(22) PCT Filed: Jan. 9, 2013

(86) PCT No.: PCT/GB2013/050030
§ 371 (c)(1),
(2) Date: Jul. 8, 2014

(87) PCT Pub. No.: WO2013/104900
PCT Pub. Date: Jul. 18, 2013

(65) Prior Publication Data
US 2014/0347043 A1    Nov. 27, 2014

(30) Foreign Application Priority Data
Jan. 9, 2012   (GB) .................................. 1200253.1

(51) Int. Cl.
G01N 27/90   (2006.01)
(52) U.S. Cl.
CPC .......... G01N 27/90 (2013.01); G01M 13/021 (2013.01); G01N 27/9046 (2013.01)
(58) Field of Classification Search
CPC ............................ G01N 27/90; G01N 27/9046
USPC ....................................................... 324/242
See application file for complete search history.

(56) References Cited

U.S. PATENT DOCUMENTS

| | | | |
|---|---|---|---|
| 4,020,678 A | | 5/1977 | Laue |
| 4,207,520 A | * | 6/1980 | Flora .................. G01N 27/9046 324/233 |
| 5,442,285 A | | 8/1995 | Zombo et al. |
| 5,670,879 A | | 9/1997 | Zombo et al. |
| 6,504,363 B1 | | 1/2003 | Dogaru et al. |

(Continued)

FOREIGN PATENT DOCUMENTS

| | | |
|---|---|---|
| EP | 2 138 836 | 12/2009 |
| JP | 2009-236767 | 10/2009 |
| JP | 2009-236767 A | 10/2009 |

(Continued)

OTHER PUBLICATIONS

International Search Report dated Mar. 18, 2013 for International Application No. PCT/GB2013/050030.

(Continued)

*Primary Examiner* — Reena Aurora
(74) *Attorney, Agent, or Firm* — Fay Sharpe LLP

(57) ABSTRACT

A method for monitoring local defects in a rotating engine component such as a gear uses one or more eddy current sensor(s) arranged to interact with the engine component as it is rotating during service. The eddy current sensor(s) may be carried by one or more teeth of a monitoring gear. A device is arranged to measure an output signal from the eddy current sensor(s) resulting from interaction with the rotating engine component. The output signal is processed so as to detect a change in shape of the output signal indicative of a local defect.

23 Claims, 11 Drawing Sheets

(56) References Cited

U.S. PATENT DOCUMENTS 8,138,755 B2 * 3/2012 Drummy ............... G01N 27/90
                                                                                    324/222
2003/0222640 A1 12/2003 Twerdochlib et al.

FOREIGN PATENT DOCUMENTS

| SU | 805097 | 2/1981 |
| SU | 1375964 | 2/1988 |
| SU | 1518628 | 10/1989 |
| SU | 1620880 | 1/1991 |
| WO | WO 2009/004319 | 1/2009 |

OTHER PUBLICATIONS

Written Opinion dated Mar. 18, 2013 for International Application No. PCT/GB2013/050030.
British Search Report dated May 10, 2012 for Application No. GB1200253.1.
K. Betzold, "Defect Characterization of a Multifrequency Eddy Current System" In: "Review of Progress in Quantitative Nondestructive Evaluation", Jan. 1, 1983, XP055397734, ISBN: 978-1-4613-3706-5 pp. 1541-1554, DOI: 10.1007/978-1-4613-3706-5_103.

* cited by examiner

FIG. 1a
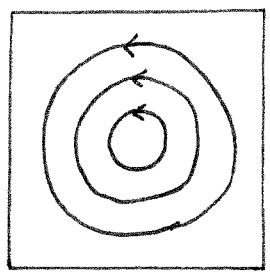
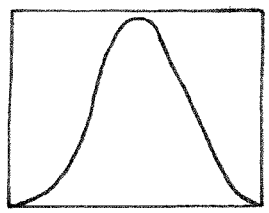
FIG. 1b
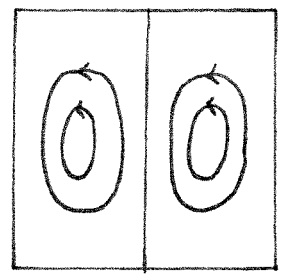
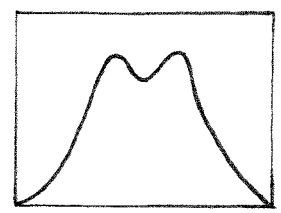
FIG. 1c
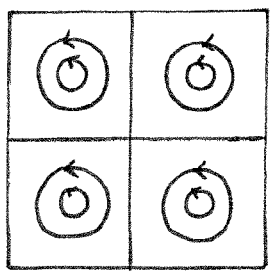
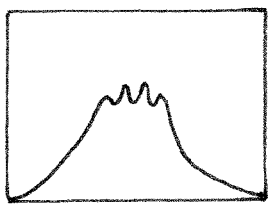
FIG. 1d
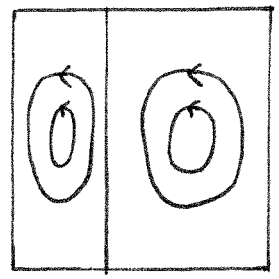
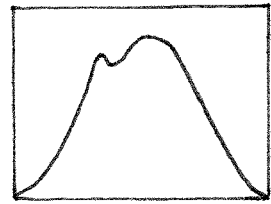

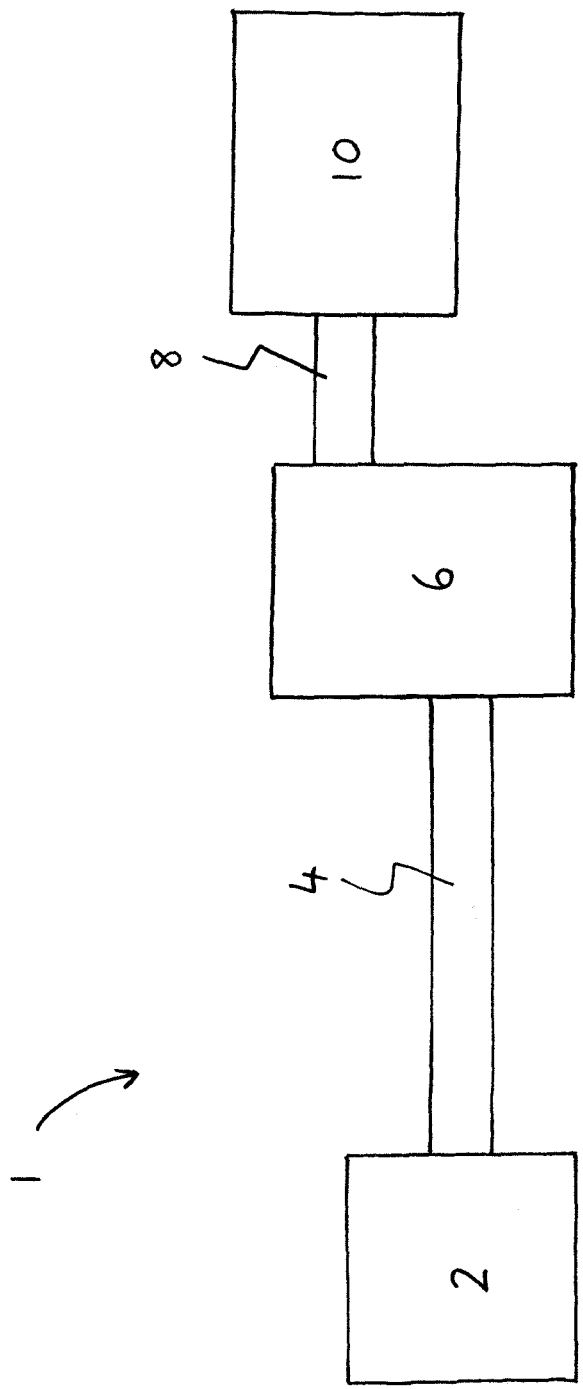

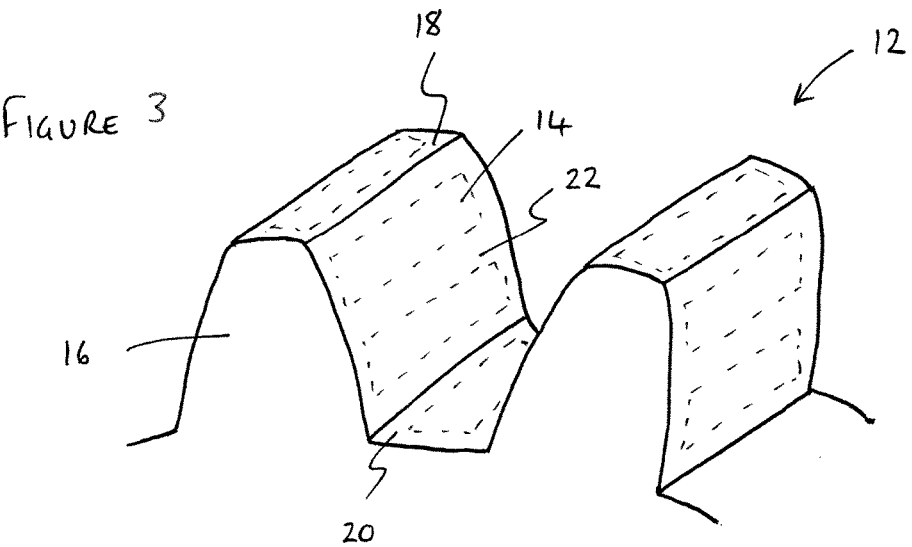
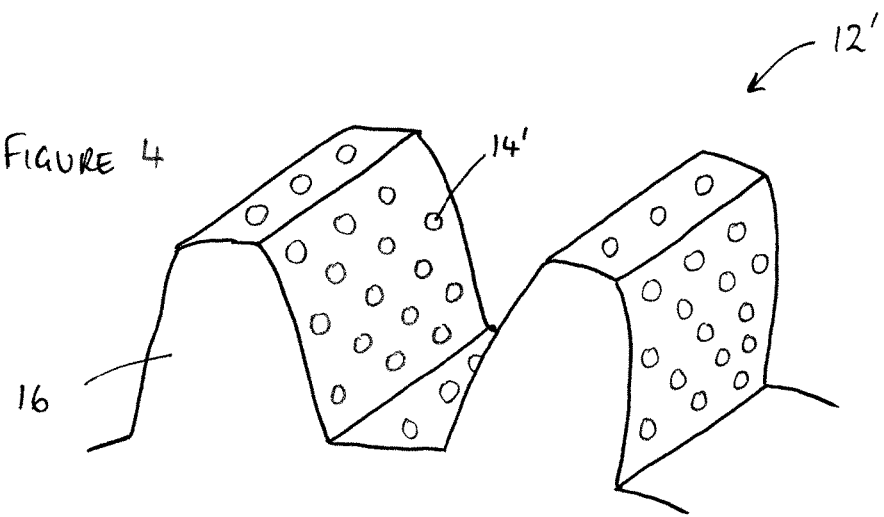

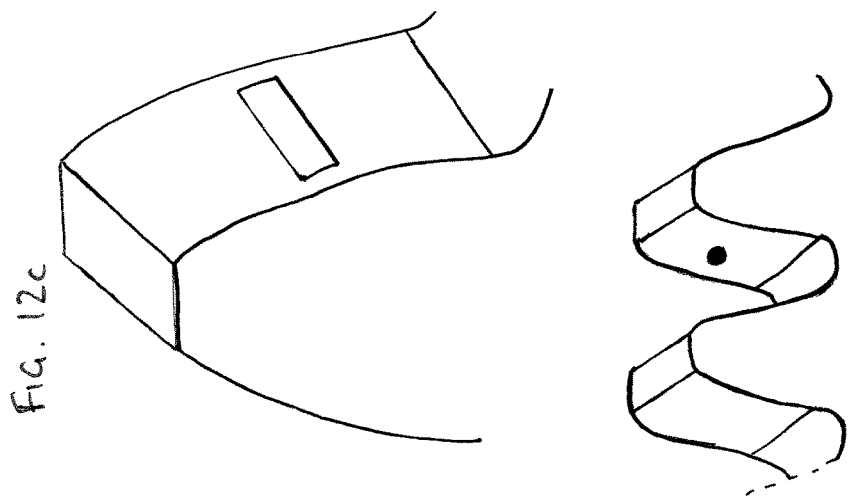
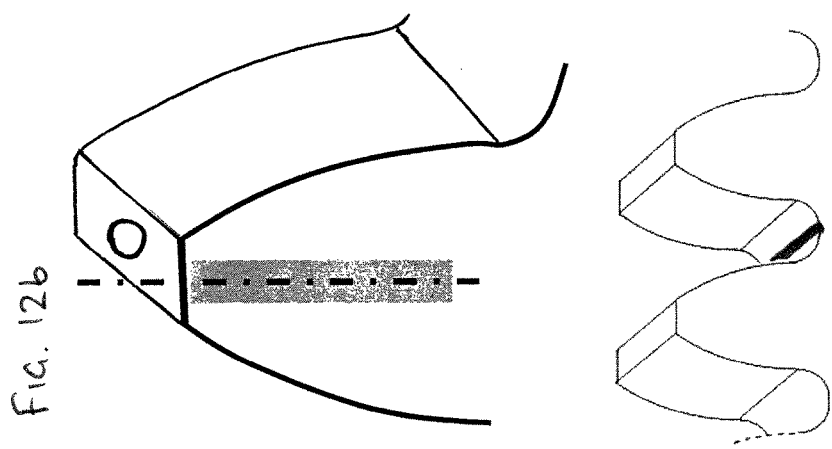
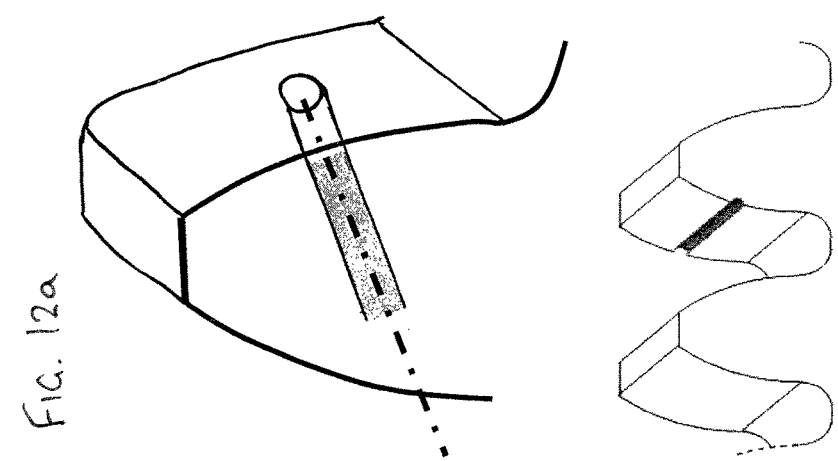

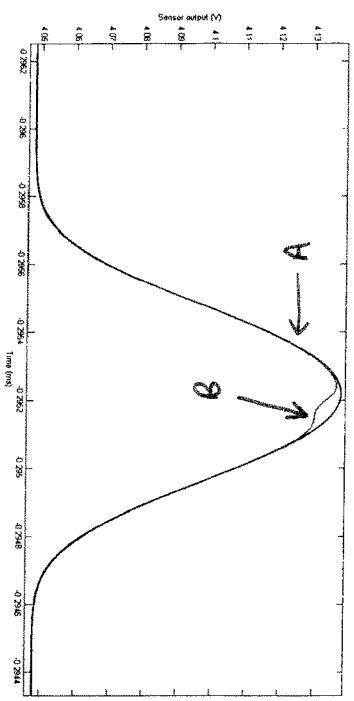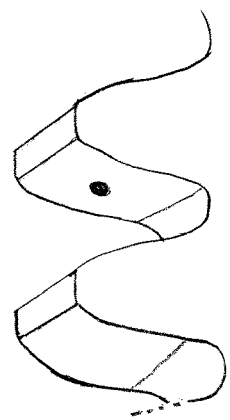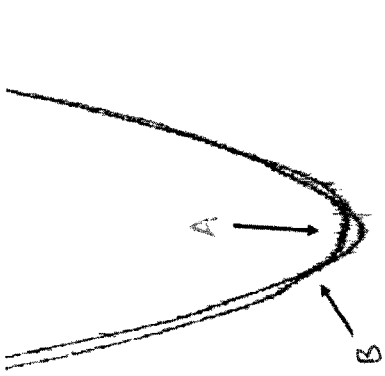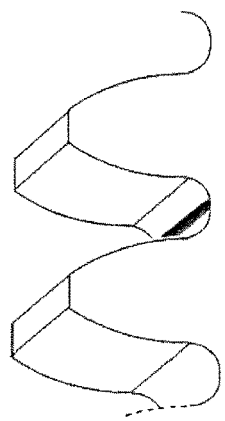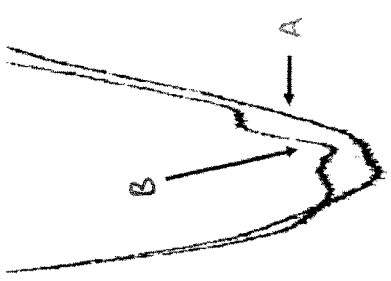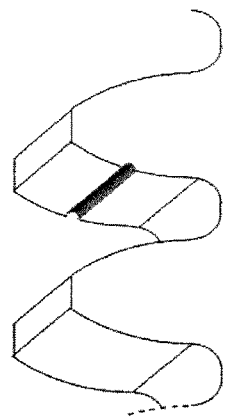
FIG. 13a  FIG. 13b  FIG. 13c

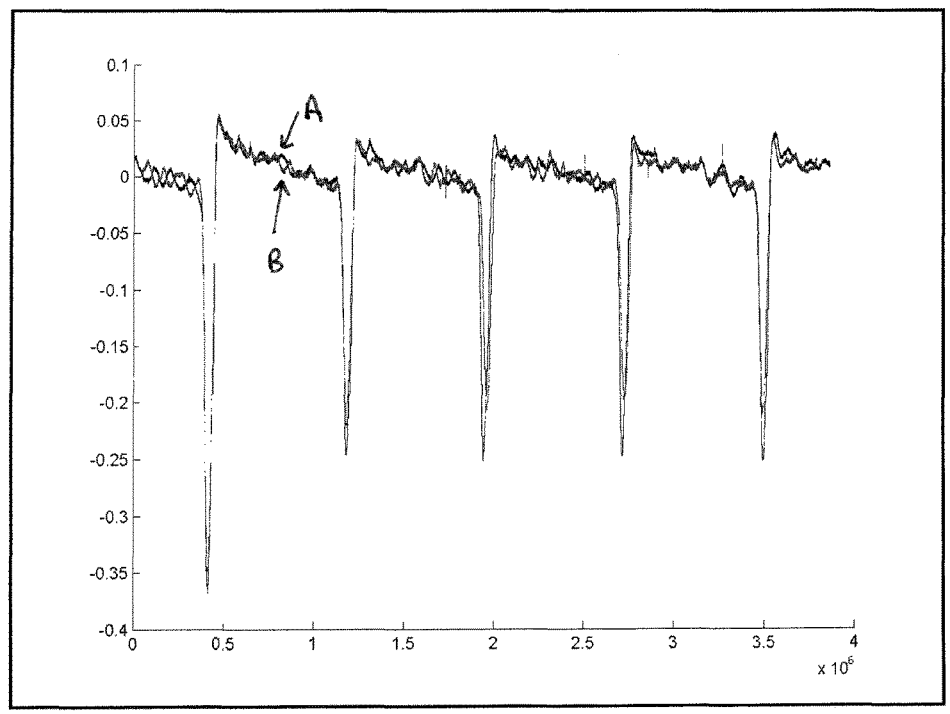
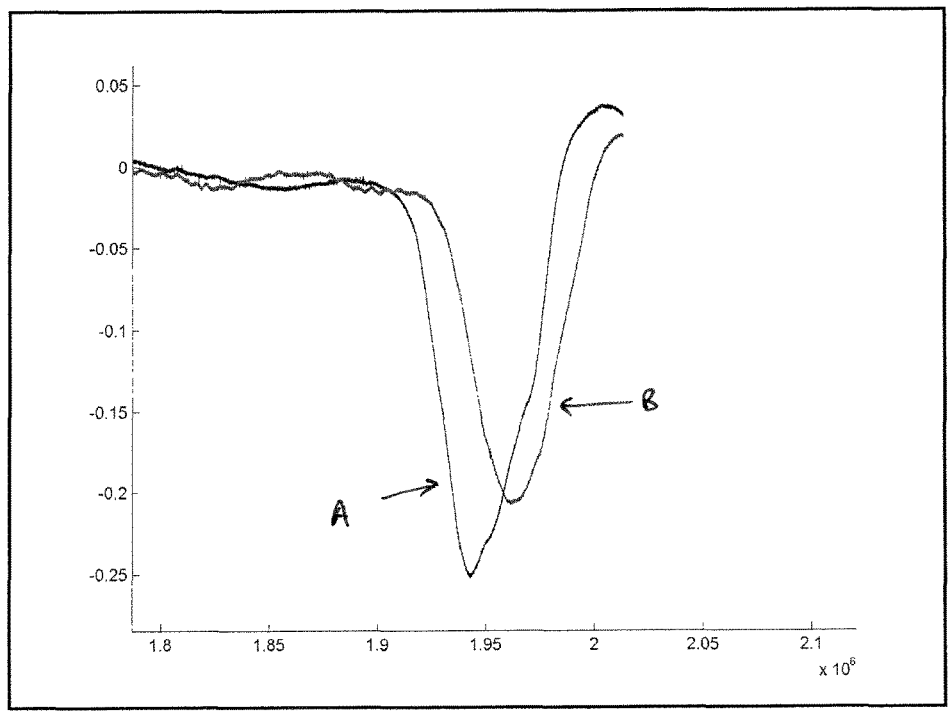
FIGURE 14

MONITORING ENGINE COMPONENTS

The present invention relates to monitoring engine components, in particular to monitoring the health of rotating components in an engine such as gears and also rotors, shafts and even blades.

The aim of engine monitoring systems is to improve operating and maintenance efficiency by reducing or eliminating component failures and unscheduled downtime. Monitoring the health of a gearbox is critical for many applications. As an example, in the wind energy industry, although the failure rate of the gearbox is lower than that of some of the other wind turbine components, the resultant downtime is greater. Repair and/or replacement of a gearbox in an off-shore wind turbine can be particularly time consuming. The cost of this downtime, together with the cost of repairs and replacement parts, make the goal of improved gearbox monitoring an important one for wind turbines and other applications. For instance, gearbox and rotor failure can be a risk for helicopters that requires close monitoring. Other applications of gearbox monitoring include the automotive industry, especially Formula One racing cars.

Current gearbox sensors diagnose its condition using measurements of e.g. the lubricating oil, abnormal vibrations, or acoustic emissions of the gearbox. For each type of measurement, many different parameters may be considered of interest and many distinct technologies can be used in an attempt to provide reliable data. For example, the lubricating oil may be analysed for the level of water content, acidity, temperature, or viscosity. In addition, the number, size or composition of metallic particles or other debris within the oil may also be analysed as these particles can provide an indication of component wear e.g. due to pitting on the surfaces of enmeshed gears. However such ex-situ techniques typically do not detect defects or wear until it is too late and the gears are already close to failure. Preventative maintenance therefore can not be scheduled in advance.

In practice, to be valuable for monitoring the health of gears, technologies must be suitable in terms of size, cost, accuracy and reliability. Furthermore, the parameter measured should desirably provide sufficient advance warning of gear failure to allow for ordering of replacement parts and scheduling of downtime and maintenance. In-service monitoring of gears, in particular of the health of the gear teeth, is difficult due to the operating environment and the meshing nature of the teeth. Optical and even capacitive sensors suffer from oil contamination making them unreliable. Optical probes in particular are vulnerable to contamination and will not work if either the light transmitter or receiver are obscured. Other sensors relying on reflection of a signal, such as radar or sonar, have similar issues and also can not provide a high enough degree of resolution to detect small surface defects such as cracks and pitting. Vibration or acoustic emission sensors are rendered insensitive by background engine vibrations. In addition, vibration and acoustic emission methods for gearbox monitoring rely heavily on statistical data analysis (time and frequency domain signal processing)—a largely manual process that is time consuming and expensive.

All current techniques for health monitoring of gearboxes have the drawback that they can only detect damage once failure is imminent. Establishing an effective maintenance regime requires a high degree of certainty from a health monitoring system if its deployment is to reduce downtime. Gearbox monitoring in particular lacks sensor technology to successfully detect tooth damage, and high speed and low speed shaft faults, in advance of failure. Vibration measurement and spectrum analysis typically chosen for gearbox monitoring are not able to detect the appearance of surface or near surface defects. Vibration signatures measure either the gearbox casing motion or the displacement of shafts in their bearings. The sensors used are usually accelerometers on the casing and proximity probes within the gearbox. Casing vibrations contain large amounts of information about the condition of the gearbox and some faults e.g. misalignment can be detected by comparing the signatures over a period of time. However, many faults are initially at high frequencies and often masked by background noise, to which the relative displacement measurements are not that sensitive. This makes it very difficult to detect wear defects such as micro and macro pitting of the gear teeth.

The present invention seeks to provide new and improved ways of monitoring the health of engine components such as gearboxes.

According to a first aspect of the present invention there is provided an apparatus for monitoring surface or near surface defects in a rotating engine component, comprising one or more inductive sensor(s) carried by a moveable member arranged to pass the sensor(s) across a portion of the surface of the rotating engine component during relative movement therebetween. Preferably the inductive sensor(s) are eddy current sensor(s) that are AC-driven at a frequency in the range of 400 kHz to 10 MHz, further preferably in the range of 1-2 MHz.

By combining a sensor with a moveable member it is possible to scan the sensor across the surface of the engine component, so that the sensor can detect local changes in the surface (or near surface) before cracks form and reach a level that can result in catastrophic failure. Using AC-driven eddy current sensor(s) at high frequencies the magnetic field is limited to probing the surface or near surface of the rotating component e.g. depths of up to 25 µm. This means that wear, such as galling on the tooth faces, can be detected. The sensor(s) provide for direct characterisation of the condition of the surface of the component and can be used alone or in combination with other sensing technologies to improve engine monitoring, for example monitoring of gearboxes and/or rotor shafts in applications such as wind turbines or helicopters. The monitoring takes place during engine operation, while the component is rotating, and thus provides a dynamic health check.

Due to the inductive nature of the sensor(s) no physical contact with the rotating engine component is necessary and additional loading can be avoided, while contamination with oil and/or dirt is not an issue. An inductive sensor detects changes in the magnetic field passing into or generated by the engine component that may be indicative of the formation of surface or near surface defects such as cracks or pitting, especially when an eddy current sensor is AC-driven at a relatively high frequency. Any engine component comprising an electrically conductive portion can be monitored by an inductive sensor. Metallic components of interest may include engine shafts and gears.

The inductive sensor(s) can use any suitable kind of magnetic field sensor such as. a solid state sensor or a coil. The inductive sensor(s) may comprise one or more solid state e.g. Hall Effect sensors to detect surface changes in a ferromagnetic e.g. iron-containing engine component. While an inductance type proximity sensor may be used to detect surface defects, it is an aim of the present invention to be able to accurately detect small scale flaws such as early stage metal loss from corrosion or erosion (e.g. macro or micro pitting). This requires an inductive sensor with sensitivity at higher frequencies. It is also desirable to be able to monitor non-ferrous components. The inductive sensor(s) preferably comprise one or more eddy current sensors. By detecting the secondary magnetic field generated by induced eddy currents, it is an advantage that such sensors can accurately detect flaws at and below the surface of a conductive material in the engine component. Any metallic engine component, or even a non-metallic e.g. plastic component with a conductive coating, can be monitored for surface defects using an eddy current sensor.

Preferably the eddy current sensor is an AC-driven (active type) sensor so that the frequency of the ac driving signal can be adjusted. Most preferably the eddy current sensor is driven by a high frequency AC excitation so as to reduce the penetration depth into the rotating component being monitored and therefore enable accurate detection of surface defects such as macro and micro pitting, and surface cracks. The eddy current sensor may be driven at a frequency in the range 400 kHz to 10 MHz, preferably at least 1 MHz up to 10 MHz, and typically in the range of 1-2 MHz.

It is an advantage of using an AC-driven eddy current sensor at relatively high frequencies, e.g. at least 500 kHz and preferably at least 1 MHz, that surface damage such as scuffing, galling, micro-pitting and macro-pitting, brinelling and spalling can be detected effectively. Such surface defects result from wear. Wear is a failure mode that can affect mechanical transmission systems at any speed. Wear is caused by the removal of material from a surface e.g. of a gear tooth, due to the sliding of adjacent components and the high stresses in the contact area between components. Poor lubrication can accelerate the accumulation of wear. In gearboxes, wear generally occurs on the teeth as these areas are subject to the greatest stress and abrasion. Root cracking can be a significant problem in aerospace gears.

An inductive sensor provides an output signal (e.g. voltage) that is proportional in amplitude to the distance between the sensor and the surface being monitored. If the surface is worn away then changes in the local separation distance can be detected as changes in signal amplitude, at least when driving the sensor at high enough frequencies to be sensitive to surface changes. For example, it is disclosed by SU-805097 to measure changes in the clearance between an inductive sensor and a tooth added to a gear wheel to determine the amount of wear on the working surfaces. However changes in signal amplitude may also result from bulk changes in the separation distance between the moveable member carrying the sensor and the rotating engine component. If, for example, the rotating engine component becomes misaligned e.g. due to failing bearings, then this could be detected as an amplitude change. Embodiments of the invention may therefore find use in monitoring bulk misalignment as well as monitoring surface or near surface defects.

The Applicant has realised that a particularly important application of the present invention may be to detect local defects in a rotating engine component before they turn into surface wear on a larger scale. It is also important to be able to distinguish surface wear from misalignment of an engine component. Static inductive sensors can be arranged in the vicinity of gears in a gearbox, for example, to monitor for misalignment. A particular advantage of using a moveable member to carry one or more inductive sensor(s) is that the sensor(s) can be arranged to pass across the surface of the rotating engine component and are therefore positioned to interact with any local defects in the component. In order to detect local defects such as cracks, brinelling, spalling, micro-pitting and macro-pitting, i.e. where material has been removed from the surface rather than a bulk change in the position of the surface, the apparatus preferably uses one or more eddy current sensor(s) and a processor to detect a change in shape of the inductive signal. The change in signal shape may be detected as well as, or instead of, a change in amplitude as discussed above.

This is considered novel and inventive in its own right, and thus according to a second aspect of the present invention there is provided a method for monitoring local defects in a rotating engine component during service, comprising: arranging one or more eddy current sensor(s) to interact with the engine component as it is rotating during service; measuring an output signal from the eddy current sensor(s) resulting from interaction with the rotating engine component; and detecting a change in shape of the output signal indicative of a local defect.

It will be appreciated that a change in shape of the output signal is independent of any bulk change in signal amplitude and the two effects can be distinguished using standard signal processing techniques. For example, MATLAB from MathWorks includes tools for signal analysis that can detect changes in shape compared to an initial set of datum signals. When an eddy current sensor interacts with a defect-free component, the eddy currents induced in the material are circular because of the circular symmetry of the field produced by the coil in the sensor. The tangential component of the field created by the eddy currents is zero at the location of the sensor. In the presence of local defects, on the other hand, the eddy currents are no longer symmetrical, and the sensor provides an output signal that has a change in shape due to the perturbed eddy currents caused by the flaw. FIG. 1 illustrates some examples of how local defects such as cracks result in a change of shape of the output signal from an eddy current sensor.

Eddy current sensors are also ideal for monitoring local defects in a rotating engine component due to their tolerance to a dirty and oil-filled environment. Such monitoring would not be possible with, say, optical or capacitance sensors because of the contamination from oil. Furthermore eddy current sensors are made small so as to increase their resolution, meaning that they can easily be fitted into a working engine for in-service monitoring of an engine component. Such monitoring can be carried out in addition to existing techniques such as vibration measurement or oil contamination monitoring. The results of monitoring for local defects can advantageously be integrated with conventional technology to enhance overall diagnosis of engine conditions and allow scheduling of downtime for maintenance.

By detecting a change in shape of the output signal it is possible to detect local defects such as pores, cracks, pits, scratches, areas of wear, etc. Faults can therefore be identified early and maintenance scheduled before the component undergoes failure. It has never previously been proposed to carry out such testing using eddy current sensors during service of a rotating engine component. A further advantage of using eddy current sensors for in-service monitoring is that the output signal can be used to detect multiple different parameters of relevance to engine health. As well as monitoring for local defects, the method preferably further comprises detecting a change in amplitude of the output signal. Amplitude changes can be used to indicate changes in surface profile and/or changes in the position of the engine component rather than local disturbances to the secondary field. Such changes may arise, for example, from misalignment, including parallel misalignment (radial or axial) and angular misalignment (yaw or pitch), or from bearing failure, unwanted vibrations, unexpected loads or overload, shaft imbalance, temperature effects, and/or manufacturing defects (e.g. concentricity and radial run-out). In fact the overall shape and amplitude of the output signal can be highly useful for diagnosing both the type of defect and location of wear resulting from engine fault. Furthermore the method can be used not only to detect the local defects themselves but also to monitor factors such as misalignment that can cause defects to develop.

It is a benefit of the invention that an engine component can be monitored throughout its service life and changes in the shape, and preferably also amplitude, of the output signal from the eddy current sensor(s) can allow defects to be detected and located before they cause a failure. The method preferably further comprises measuring a datum output signal from the eddy current sensor(s) when the rotating engine component is initially installed, and detecting a change in shape of the output signal by comparison to the datum output signal. Further preferably a change in amplitude of the output signal is detected by comparison to the datum output signal. An advantage of detecting any amplitude change (e.g. due to radial movement of a shaft carrying the engine component due to bearing wear etc.) is that this can be used to normalise the datum output signal and then any changes in shape can be detected more easily. Long term comparison of the output signals with the datum measurement can allow engine health to be predicted so that maintenance can be planned ahead.

Eddy current sensors can have a wide frequency response, from DC to the megahertz range. According to a set of embodiments the method may comprise driving the eddy current sensor(s) at a DC frequency. Mechanical transmission systems such as gearboxes can fail due to fatigue caused by excess loading, which leads to defects that penetrate much deeper than the surface. Fatigue is caused by repeated cycling of loads that are within the elastic limit of a component's material, resulting in progressive damage to a localised area experiencing the greatest strain. Fatigue failure occurs in three stages: crack initiation, propagation and then complete fracture. Such fatigue cracks can result in rapid failure of a rotating component. Local cracks in the root or surface of teeth in a gear wheel are readily detected by an eddy current sensor as soon as they form and gearbox maintenance may therefore be scheduled before a serious failure is allowed to occur. A DC-driven eddy current sensor may be used when monitoring for deeper flaws such as cracks. To detect deep cracks, it may be preferable to use a sensor with a larger diameter coil to increase the penetration of the eddy currents in the component being monitored.

According to another set of embodiments the method may comprise driving the eddy current sensor(s) at an AC frequency chosen from one or more of: (i) at least 1 kHz; (ii) at least 100 kHz; (iii) at least 500 kHz; (iv) at least 1 MHz; (v) at least 2 MHz; and (vi) up to 10 MHz. The depth of penetration of the eddy currents induced by a sensor is related to frequency according to $\delta=1/\sqrt{(\sigma\mu_0\mu_r f)}$, where $\delta$=depth of penetration, $\sigma$=electric conductivity of the material of the engine component being monitored, $\mu_0$=absolute permeability, $\mu_r$=relative permeability, and f=frequency. It is possible to probe different depths of a component of interest by changing the frequency. The Applicant has recognised that the frequency used to drive the eddy current sensor(s) can be selected or adjusted to target different kinds of local defect, for example a lower frequency for deep flaws and a higher frequency for surface flaws. It is therefore preferable that the method further comprises adjusting the frequency at which the eddy current sensor(s) are driven, e.g. to monitor for different local defects and/or to investigate the depth of flaws.

Non ferromagnetic materials have relative and absolute permeability values of 1. The depth of penetration can therefore be adjusted to a large degree by changing the frequency. Ferromagnetic materials, on the other hand, have relative and absolute permeability values far larger than 1. Although the driving frequency can still be adjusted to change the depth of penetration, the method is most sensitive to surface and near surface defects in the carbon steel materials typically used for engine components i.e. the "skin effect". As is mentioned above, it is an advantage of using an AC-driven eddy current sensor comprising a coil that is driven at relatively high frequencies, preferably at least 500 kHz and further preferably at least 1 MHz, that surface damage such as scuffing, galling, micro-pitting and macro-pitting, brinelling and spalling can be detected effectively. A further advantage of driving the eddy current sensor(s) at higher frequencies e.g. at least 1 MHz is that changes in the amplitude of the output signal can be attributed to local changes in the surface of the component due to wear rather than bulk misalignment in the engine. Where the rotating engine component has multiple surfaces in close proximity to be measured, e.g. the surfaces of teeth on a gear wheel, then a high driving frequency can also ensure that the secondary fields do not penetrate deep enough to interact from one surface to another.

According to another aspect of the present invention there is provided an apparatus for monitoring local defects in a rotating engine component during service, comprising one or more eddy current sensor(s) arranged to interact with the engine component as it is rotating during service, a device arranged to measure an output signal from the eddy current sensor(s) resulting from interaction with the rotating engine component, and a processor arranged to detect a change in shape of the output signal indicative of a local defect.

For the reasons already outlined above, the processor is preferably arranged to detect a change in amplitude of the output signal. Changes in both shape and amplitude of the output signal may therefore be detected. Preferably the device is arranged to measure a datum output signal from the eddy current sensor(s) when the rotating engine component is initially installed, and the processor is arranged to detect change in shape (and optionally amplitude) of the output signal by comparison to the datum output signal.

In a set of embodiments the apparatus preferably comprises a driver arranged to drive the eddy current sensor(s) at a DC frequency. In another set of embodiments the apparatus preferably comprises a driver arranged to drive the eddy current sensor(s) at an AC frequency chosen from one or more of: (i) at least 1 kHz; (ii) at least 100 kHz; (iii) at least 500 kHz; (iv) at least 1 MHz; (v) at least 2 MHz; and (vi) up to 10 MHz. The driver may be arranged to adjust the frequency at which the eddy current sensor(s) are driven, e.g. to monitor for different local defects and/or to investigate the depth of flaws.

In such apparatus the eddy current sensor(s) may be arranged in any suitable way to interact with the engine component as it is rotating during service. The sensor(s) may potentially be static. However, a problem with using static sensors is that it may be difficult for them to be arranged close enough to the rotating component for eddy currents to be induced without interfering with the rotation. In a preferred set of embodiments the one or more eddy current sensor(s) are carried by a moveable member that is arranged to pass the sensor(s) across a portion of a surface of the rotating engine component during relative movement therebetween. As is described in relation to the first aspect of the invention outlined above, this can make it much more practical for the sensor(s) to scan across the surface of the engine component as it is rotating during service. The sensor(s) may, for example, be carried by another component that is driven by the same shaft as the engine component or by another rotating shaft in the engine.

Eddy current sensors of various forms are known for ex-situ testing of engine components made of conductive e.g. metallic or metal-coated materials. In one set of embodiments the eddy current sensor may be of the passive type, e.g. where the primary magnetic field is generated by a permanent magnet and its variations caused by eddy currents in the conductive component are sensed by an associated coil. In another set of embodiments the eddy current sensor may be of the active type, dc- or ac-driven, e.g. where the primary magnetic field is generated by one or more current-carrying coils and the secondary fields produced by resultant eddy currents in the conductive component are sensed by the same or different coil(s). Preferably the eddy current sensor is of the active type with the same coil used for both generating the primary magnetic field and sensing the secondary magnetic field, so that the sensor is both structurally compact and light in weight.

It has been recognised that to achieve good resolution with an eddy current sensor requires a narrowly-defined magnetic flux region. The magnetic flux region is larger than the coil diameter so a high resolution requires a small coil. However the coil size also determines the range of the sensor, with a typical eddy current sensor having a range that is approximately half the coil diameter. It is an advantage of various embodiments of the present invention that the sensor is carried by a moveable member which can be moved close to the surface of a rotating component being monitored, so that the range of the sensor does not need to be large and it can provide a good resolution for detecting small surface (and near surface) defects such as cracks and pitting. Furthermore the moveable member can be used to traverse the sensor across at least a portion of the surface of the rotating component, so that the effective range of the sensor is increased.

So as to improve the resolution of the eddy current sensor, preferably the sensor comprises a common coil for use in both generating a primary magnetic field and detecting the effect of eddy currents generated by the primary magnetic field in a rotating component being monitored, wherein the coil is elongate in section. When the sensor coil is wound on a former of elongate section, say rectangular or elliptical, the range of the sensor is equivalent to that of one with a circular coil of the same number of windings and a diameter equal to the elongate dimension of the coil, but its resolution is improved in terms of the detection of elongate features such as cracks which are generally aligned with the elongate dimension of the sensor. In order to improve the detection of cracks and other flaws which may extend in different directions across a surface, the moveable member may carry multiple elongate sensors with at least a pair of elongate sensors arranged substantially perpendicular to one another.

The apparatus e.g. the moveable member may carry a single sensor, for example shaped and/or sized to match a portion of the rotating component being monitored. However resolution may be improved by providing multiple smaller sensors rather than a single sensor. The moveable member may carry an arrangement of two, three, four, five, six, or any number of sensors in an array. The array can be arranged so as to scan across a representative portion of the rotating component, for example across its width, with high resolution. The sensors in an array may have one or more different orientations so as to improve the detection efficiency for flaws in different directions.

The sensor(s) may be carried on the surface of the moveable member so as to maximise the sensitivity of the sensor(s). However, in one preferred set of embodiments the sensor (or an array of multiple sensors) is mounted below the surface of the moveable member, so as to be protected from the external environment. Where the moveable member comes into physical contact with a rotating component being monitored then this can protect the sensor(s) from wear. Taking into account that the output of an inductive sensor depends in part on the distance between the rotating component being monitored and the sensing coil, each sensor— or at least its coil(s)—is preferably provided within the moveable member but still close to the surface that is brought into range of the rotating component. Preferably the sensor(s) is/are integrated into the moveable member. The magnetic fields generated by an inductive sensor, such as an eddy current sensor, are capable of penetrating through the moveable member provided it is not predominantly composed of ferromagnetic material. A metal member made of aluminium or any non-ferrous alloy may be used. Preferably the moveable member, or at least that part of the moveable member surrounding the sensor(s), is formed of a non-conductive material so as to avoid signal attenuation. A suitable polymer may be used.

The speed of movement of the moveable member relative to the rotating component can be selected so as to achieve a desired surface scanning rate. It is a particular advantage of the invention that the speed of the moveable member allows the sensor scanning rate to be controlled, whereas a stationary sensor monitoring the surface of a rotating component is forced to scan across the surface at the component's speed of rotation.

The moveable member can be moved in any way suitable for passing the sensor across a selected portion of the surface of the rotating engine component. In some embodiments the moveable member may be arranged so as not to contact the surface of the component being monitored. This can help to ensure that the monitoring process does not unduly cause or add to wear of the surface being monitored. In other embodiments the member may move so as to come into contact with the surface being monitored, thereby bringing the sensor(s) into close contact, if not direct physical contact, with the surface of the component being monitored. This can improve the sensitivity of the signal(s) from the sensor(s).

The moveable member may move linearly or even in a zig-zag manner. For example, it can be envisaged that the sensor member be arranged to traverse across the width of the top land of a gear tooth as each tooth of a rotating gear wheel passes by. Or, the sensor member could be arranged to move in towards the bottom land between the teeth and out as each tooth passes by, so as to scan down the face of the teeth and attempt to monitor the surface of the bottom lands. However, such linear movements may not be well adapted to scanning the various external surfaces of a rotating member having a complex shape, such as a toothed gear wheel.

Preferably the moveable member is a rotating member. This means that the sensor(s) carried by the moveable member can be moved on a complementary trajectory to the surface of the rotating component being monitored. When the moveable member is rotating it can be easier to bring the sensor(s) into close contact, if not direct physical contact, with the surface of the monitored component.

As is mentioned above, the engine component may be any rotating component such as a rotor shaft, bearing, transmission coupling or even a turbine blade. For example, the apparatus may be used to monitor a platform at the bottom of a blade where cracks can develop, e.g. in a low-speed engine rotor. In a preferred set of embodiments the rotating engine component is a gear and the moveable member is shaped so as to enmesh with the gear. The moveable member may take the form of a monitoring gear or part of a monitoring gear. The moveable member may therefore comprise one or more teeth. While the sensor(s) may be carried in the main body of a toothed monitoring gear, for example to examine the surface of the top lands of gear teeth, a benefit can be achieved by arranging the sensor(s) in or on a tooth or teeth that enmesh with the teeth of the gear being monitored. Advantageously this provides very intimate contact between the monitoring gear and the monitored gear so that the sensor(s) can have access to the various surfaces of the gear teeth. Preferably the one or more sensor(s) are carried by one or more teeth of the monitoring gear. The invention is well suited to monitoring for gear tooth wear because the monitoring gear allows the sensor(s) to traverse across the surface of the gear teeth, scanning different parts of a tooth as the gears enmesh, as well as obtaining a signal from each tooth of the monitored gear. A particular benefit of carrying sensor(s) in or on a monitoring gear is that the close contact between the gear teeth enables the inner surfaces and corners of gear teeth to be tested in-situ in a way not previously possible.

At least one tooth of the monitoring gear may be provided with one or more sensors. Even if only one tooth of the monitoring gear carries the sensor(s), the ratio between the number of teeth on the monitoring gear and the number of teeth on the gear being monitored can be selected to ensure that every tooth of the monitored gear is tested after a certain number of revolutions. For example, when the monitoring gear is an integer different in gear teeth number to the gear wheel being inspected the sensor(s) progressively scan every tooth in succession. This has the advantage of only one sensor signal (or one set of signals) requiring transmission, rather than multiple teeth of the monitoring gear collecting signals at the same time. Depending on the gear ratio, a single sensing tooth can adequately scan each tooth of the monitored gear frequently enough that changes in the baseline i.e. datum signal over time can be assessed and used to generate an alert when the first signs of damage are detected. In other embodiments, a plurality of the teeth of the monitoring gear may each carry one or more sensors so as to increase the frequency of testing of the teeth of the monitored gear. The sensor(s) carried by different teeth may each have a different position so that different teeth of the monitoring gear scan different surface portions of the monitored gear and its teeth. In addition, or alternatively, the sensor(s) carried by different teeth may have one or more different orientations so that different types of defect can be monitored, As is mentioned above, the sensor(s) may be provided in an array to increase the overall detection range. In embodiments where the moveable member takes the form of a monitoring gear, multiple sensors may be arranged in or on a tooth of the monitoring gear so as to provide for accurate sensing across the various surfaces of the teeth of a gear being monitored, including the top land, face, flank, fillet and/or bottom land. Thus a tooth of the monitoring gear may carry one or more of: a sensor with its field penetrating the top land, a sensor with its field penetrating a face and/or flank of the tooth, and a sensor with its field penetrating the bottom land. Multiple sensors per tooth will likely facilitate such an arrangement. However a single sensor may be provided in or on a tooth of the monitoring gear having a multi-directional field that monitors different tooth surfaces. In other embodiments it may be preferable to avoid different tooth surfaces being monitored by the same sensor, and thus a tooth may have a sensor arranged therein such that its field penetrates one face but not another. For example, the length of the sensor may be limited so that its field can not penetrate both faces of the tooth. This can help to ensure that the signals from different surfaces can be distinguished from one another.

Similarly, in embodiments where a tooth carries multiple sensors, e.g. to monitor the same surface, it may be preferable to maintain a minimum spacing between the sensors so that their fields do not overlap. Of course, it will be appreciated that the fact the monitoring gear is rotating and there is relative movement between its teeth and those of the monitored gear means that the sensor(s) or any arrays of sensors do not need to have a range extending across the entire surface of a tooth. As the teeth of the monitoring gear enmesh with the teeth of a monitored gear the range of a given sensor is scanned across a portion of the surface. This enlarges the effective sensor range so that the number and/or size of sensors required can be minimised.

The shape and/or size of the or each sensor may be designed or chosen to match the shape of the moveable member, especially when the moveable member is a toothed gear and the sensor(s) are carried by one or more teeth. For example, an elongate sensor may be arranged to have an elongate dimension substantially matching the width of a tooth; as the monitoring gear enmeshes with a gear being monitored the sensor will traverse across the face and flank of each tooth so as to effectively cover the whole side surface with a single sensor. Furthermore, the shape of the sensor(s) can be tailored to the rotating component being monitored and arranged to provide a magnetic field that is optimised for the detection of certain expected defects or specific failure modes. For example, at least some of the sensor(s) may be chosen to be relatively small for scanning a surface portion that is expected to have small-scale defects, such as micro pitting, that require a high resolution to be detected. At least some others of the sensor(s) may be chosen to be relatively large for monitoring macro changes in the position of the surface portion being monitored, for instance due to misalignments or mechanical faults in the engine. In practice a moveable member may be designed to monitor a given engine component using a number of different sensors, the sensors differing in terms of size, shape and/or mounting position, including being mounted in different orientations.

The moveable member may be provided by any transmission gear, such as a driving gear, follower gear and/or idler gear, in the engine, e.g. one of the working gears in a gearbox. The working gears may therefore be self-monitoring with the sensor(s) scanning the surface of one or more teeth as the gears enmesh during rotation. In such embodiments the invention may be carried out by mounting one or more sensors on or in the teeth or body of an existing gear in a gearbox to be monitored. This removes the need for space in the gearbox to accommodate the sensing apparatus. However, it has been appreciated that working gears are typically designed to bear substantial loads as they transmit rotation through a gear train and the attachment or integration of sensor(s) could risk weakening a gear, especially the teeth, as well as subjecting the sensor(s) to loads that could interfere with their operation. It is therefore preferable that the moveable member takes the form of a monitoring gear (or at least part of a monitoring gear) that is a non-working gear, i.e. a gear that does not drive any part of the transmission system but merely rotates in engagement with one or more transmission gears being monitored. By providing a dedicated monitoring gear to carry the sensor(s) the teeth of the monitoring gear will enmesh with the teeth of a transmission gear being monitored, providing close contact across the surfaces of the gear teeth, but without substantial loads being transmitted to the monitoring gear. A further advantage is that the monitoring gear can be removed or replaced, for example to repair or replace the sensor(s), without affecting the transmission gears in a gearbox.

Preferably the apparatus further comprises a wired, or preferably wireless, data transfer telemetry system to transfer sensor signals e.g. from the member's moving frame of reference to a stationary frame of reference outside the apparatus. The moveable member may comprise an electronic signal processing system e.g. to carry out local signal analysis before data transfer. Alternatively, the raw signal data may be transferred by the telemetry system to an external processor. The telemetry system may be connected to a control and/or display unit to provide monitoring information. The monitoring information may be used by an operator to determine when to schedule maintenance of the component being monitored. A control unit may even use the monitoring information to automatically adjust one or more parameters relating to engine operation.

It will be appreciated that various embodiments of the present invention can provide for very reliable and early detection of defects in an engine component such as a gear. One of the most important components in a wind turbine is the gearbox. Placed between the main shaft and the generator, its task is to increase the slow rotational speed of the rotor blades to the generator's rotational speed of 1000 or 1500 rpm. The present invention may find particular application in gearbox monitoring for wind turbines. Embodiments of the present invention can also provide an early warning system for engine failure in helicopters. In a helicopter the main drive shaft is located between the engine and the rotor gearbox to transmit engine power, while a rotor shaft transmits power from the gearbox to the propeller. A failure in any of the drive shaft, gearbox and/or rotor shaft has the same effect as an engine failure, because power is no longer provided to rotate the propeller. It is therefore critical to be able to detect changes in these components so that maintenance can be carried out before a failure condition is likely to develop.

According to a further aspect of the present invention there is provided a method of monitoring a gearbox in a wind turbine or helicopter comprising providing one or more monitoring gear(s) in the gearbox that carry one or more inductive sensor(s), the monitoring gear(s) engaging with one or more transmission gears to be monitored so as to pass the sensor(s) across the surface of the transmission gears during their rotation. Preferably the inductive sensor(s) are eddy current sensor(s), further preferably with any of the features already described above. In particular, the eddy current sensor(s) may be AC-driven at a frequency in the range of 400 kHz to 10 MHz, preferably in the range of 1-2 MHz. Such methods are well suited for monitoring surface or near surface defects in the transmission gears.

In a preferred embodiment the method comprises measuring an output signal from the eddy current sensor(s) and detecting a change in shape of the output signal indicative of a local defect in the one or more transmission gears. Preferably the method further comprises detecting a change in amplitude of the output signal. Changes in both shape and amplitude of the output signal may therefore be detected so that various different kinds of defect, and their location, can be monitored during service of a transmission gear in a gearbox.

According to a yet further aspect of the present invention there is provided a method of monitoring for surface or near surface defects in a rotating engine component using a moveable member carrying one or more inductive sensor(s), comprising moving the member relative to the rotating component so as to pass the sensor(s) across a portion of the surface of the rotating engine component. Preferably the inductive sensor(s) are eddy current sensor(s) that are AC-driven at a frequency in the range of 400 kHz to 10 MHz, further preferably in the range of 1-2 MHz.

The invention therefore extends to methods of nondestructive testing that take place in situ, while an engine component such as a gear is rotating. As compared to standard methods for monitoring component operation using a proximity sensor to measure the rotational speed, the inductive sensor(s) are not stationary during testing. Instead, movement of the member carrying the sensor(s) ensures that the sensor(s) are scanned across a portion of the surface of the component being monitored. Changes in the surface topography indicative of the development of flaws such as cracks or pitting can therefore be detected. The rotating engine component may comprise a gearbox or rotating shaft in an engine. Applications of a monitoring method or apparatus according to embodiments of the present invention may include power generation e.g. wind turbine gearboxes, marine, aerospace, helicopters, and automotive e.g. Formula One cars.

Any of the apparatus features described hereinabove may also be provided as preferred features of such methods. Furthermore, any one or more of the apparatus features may be taken in combination with one or more other features in accordance with embodiments of any of the aspects of the invention.

Some preferred embodiments of the present invention will now be described, by way of example only, and with reference to the accompanying drawings, in which:

FIG. 1a illustrates the eddy currents induced by a cylindrical sensor and its output signal for a square token without any local defects present, FIG. 1b illustrates how the output signal is changed when the eddy currents are disturbed by a crack, FIG. 1c illustrates how the output signal is changed when the eddy currents are disturbed by two cracks, and FIG. 1d illustrates how the output signal is changed when the eddy currents are disturbed by an off-centre crack;

FIG. 2 is a schematic block diagram of the main components in a wind turbine engine transmission system;

FIG. 3 is a partial perspective view of a monitoring gear according to an embodiment;

FIG. 4 is a partial perspective view of a monitoring gear according to another embodiment;

FIGS. 12a to 12c show different eddy current sensor designs in the teeth of a monitoring gear and FIGS. 12d-12f show seeded defects in a gear wheel being monitored;

FIGS. 13a to 13c show the measured or predicted output signals of the eddy current sensors of FIGS. 12a to 12c;

FIG. 14 shows the output signal from the eddy current sensor design of FIG. 12a when monitoring a gear with surface galling.

Figure 5:
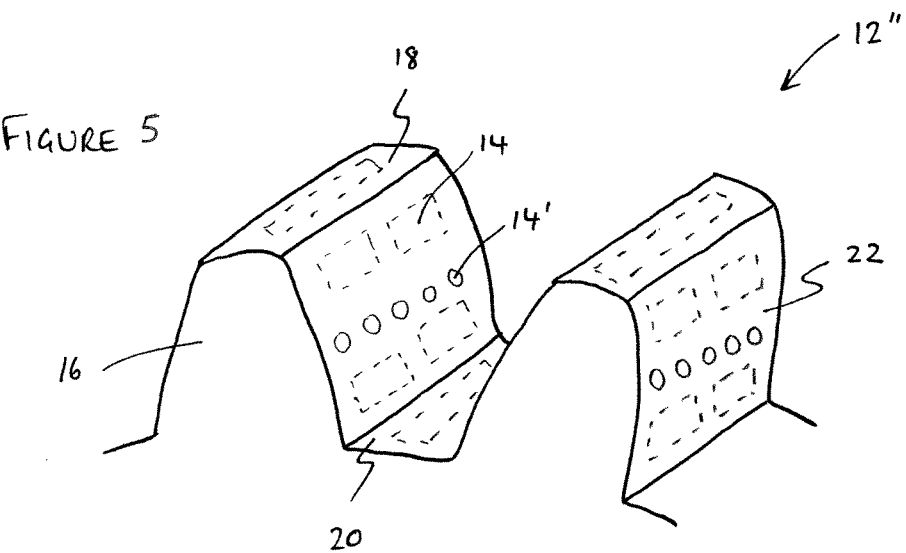
FIG. 5 is a partial perspective view of a monitoring gear according to yet another embodiment.

Some preferred embodiments will be described in the context of a gearbox in a wind turbine transmission system, for example as shown in FIG. 2. It can be seen that the transmission system 1 comprises a wind turbine hub 2 mounted on a main rotor shaft 4. The turbine hub 2 includes the blades, vanes or other rotary arrangement that collects wind power. While the rotor shaft 4 is schematically shown as being horizontal, the turbine may be of the horizontal- or vertical-axis type. It will be appreciated that such a transmission system could instead be provided for a helicopter propeller mounted on a rotor shaft, but with power being transmitted in the opposite direction.

A gearbox 6 converts the slow rotational speed of the main rotor shaft 4, e.g. 30-40 rpm, into a suitable output speed, e.g. 1000-1500 rpm. The gearbox 6 may comprise one or multiple stages of normal gears and/or planet gears. The gearbox 6 has an output shaft 8 that drives a generator 10. Inside the gearbox 6, at least one gear wheel is provided with inductive sensors for monitoring purposes. This monitoring gear may be one of the working gears, e.g. a driving, follower or idler gear, that is transmitting torque from the main rotor shaft 4 to the output shaft 8. Or the monitoring gear may be a non-working gear that does not drive any part of the transmission system but merely rotates in engagement with one or more transmission gears being monitored.

There is seen in FIGS. 3 to 6 some embodiments of a monitoring gear 12. In FIG. 3 the gear 12 is shown as having elongate sensors 14 that extend across the width of the teeth 16. A sensor 14 is provided for the top land 18, another sensor 14 for the bottom land or root 20, and two sensors for the flank 22 of each tooth 16. In FIG. 4 the gear 12' is shown as having relatively small sensors 14' provided for the various surfaces of the teeth 16. In FIG. 5 the gear 12" is shown as having a mixture of elongate sensors 14 and small sensors 14'. The elongate sensors 14 are carried by the top land 18 and bottom land 20 of each tooth 16, where a high resolution may not be required. On the flanks 22 of the teeth 16 a row of small sensors 14' is provided along the pitch line where the contact load is maximum and defects are most likely to form. The small sensors 14' provide a higher resolution so that flaws can be detected early in this region. The flanks 22 are also provided with some larger rectangular sensors 14, arrayed in pairs above and below the pitch line.

It will be appreciated that the number of sensors and their arrangement in a monitoring gear 12 can take many different forms, typically tailored to the gears being monitored and the sensitivity required. While multiple teeth 16 of a monitoring gear 12 have been shown to be provided with sensors 14, 14', it may be sufficient to instrument just a single tooth, or only certain ones of the teeth. This may be dictated by the speed of rotation of the gears involved. Also it may be sufficient to provide sensors for only some surfaces of the teeth 16. Different teeth 16 may be provided with sensors for different surfaces.

Figure 6:
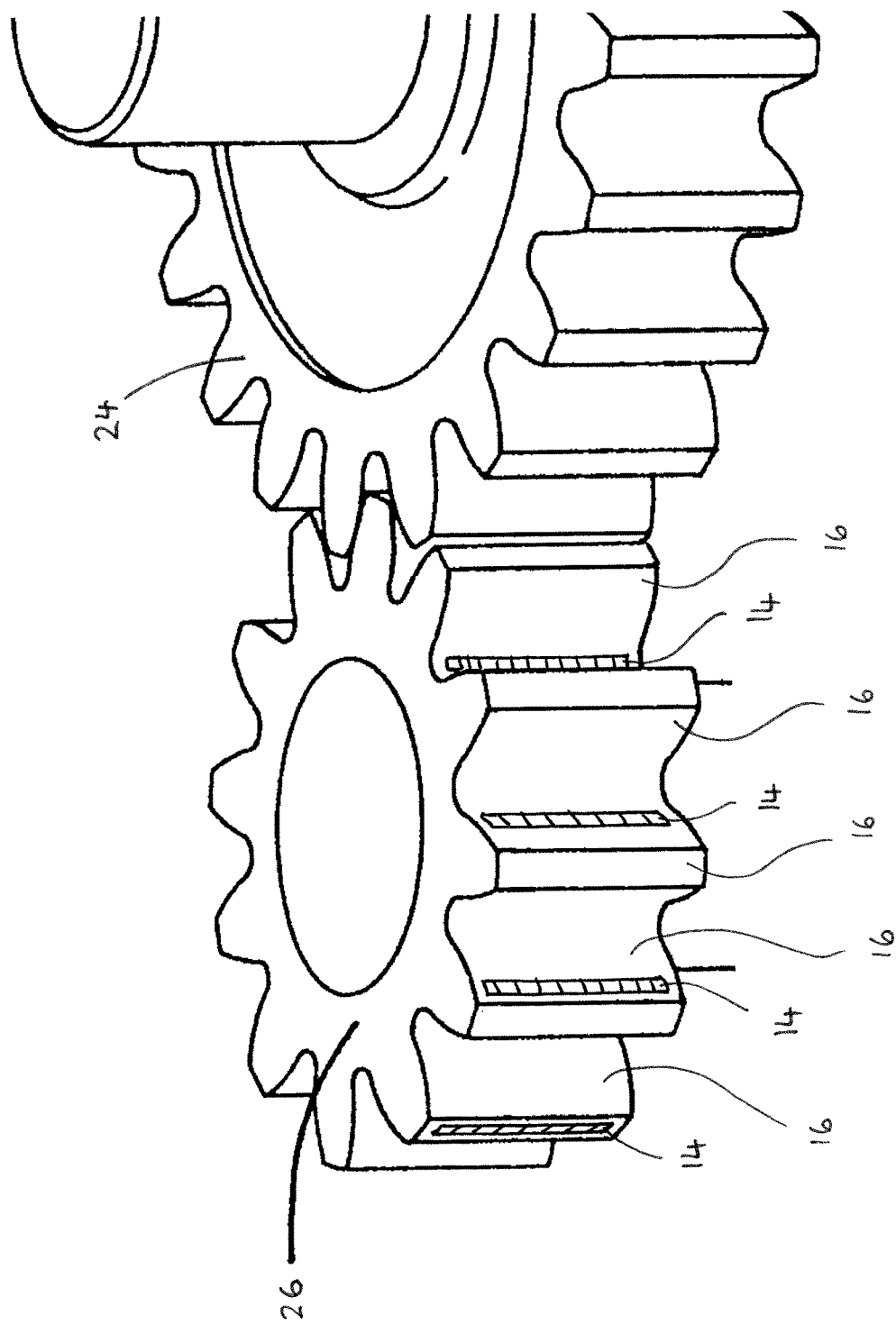
FIG. 6 is a partial perspective view of a monitoring gear according to yet a further embodiment.

FIG. 6 shows another embodiment of a monitoring gear 26 that has a single elongate sensor 14 carried by each tooth 16, or in the flank between teeth 16. The position of the elongate sensor 14 is different for each of the teeth 16. The monitoring gear 26 may be formed to have a different number of teeth to an adjacent gear 24 being monitored. This means that each of the teeth 16 mesh with the those of the other gear 24 after a number of revolutions. The sensors 14 in the different positions ensure that the various surfaces of the teeth are sequentially scanned without using a large number of sensors.

The inductive sensors may be eddy current sensors comprising a coil wound on a former. The shape of the former, for example cylindrical or rectangular, can be chosen depending on the desired shape of the sensor. The former may provide a core for the coil that is ferromagnetic or insulative. The coil is connected to a DC or AC power supply and has an output line for connection to a signal unit. The coil may typically be driven by an AC signal at a frequency of 1-2 MHz.

Figure 7:
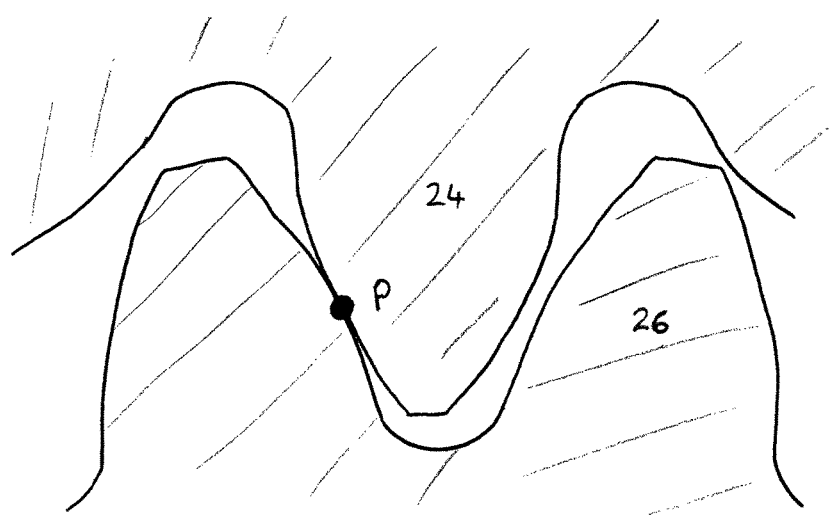
FIG. 7 is a schematic cross-sectional view of meshing gears.

FIG. 7 is a cross-sectional diagram of a driving gear 24 meshing together with a follower gear 26. The kinematics of gear meshing involve both sliding and rolling contact, with pure rolling occurring at the pitch line indicated by the pitch point P. The loads become a maximum as the contact point moves into the vicinity of the pitch line. A monitoring gear 12 may carry one or more sensors to examine the surface of such gears 24, 26, preferably arranged to detect the flaws that typically develop around the pitch line.

Figure 8:
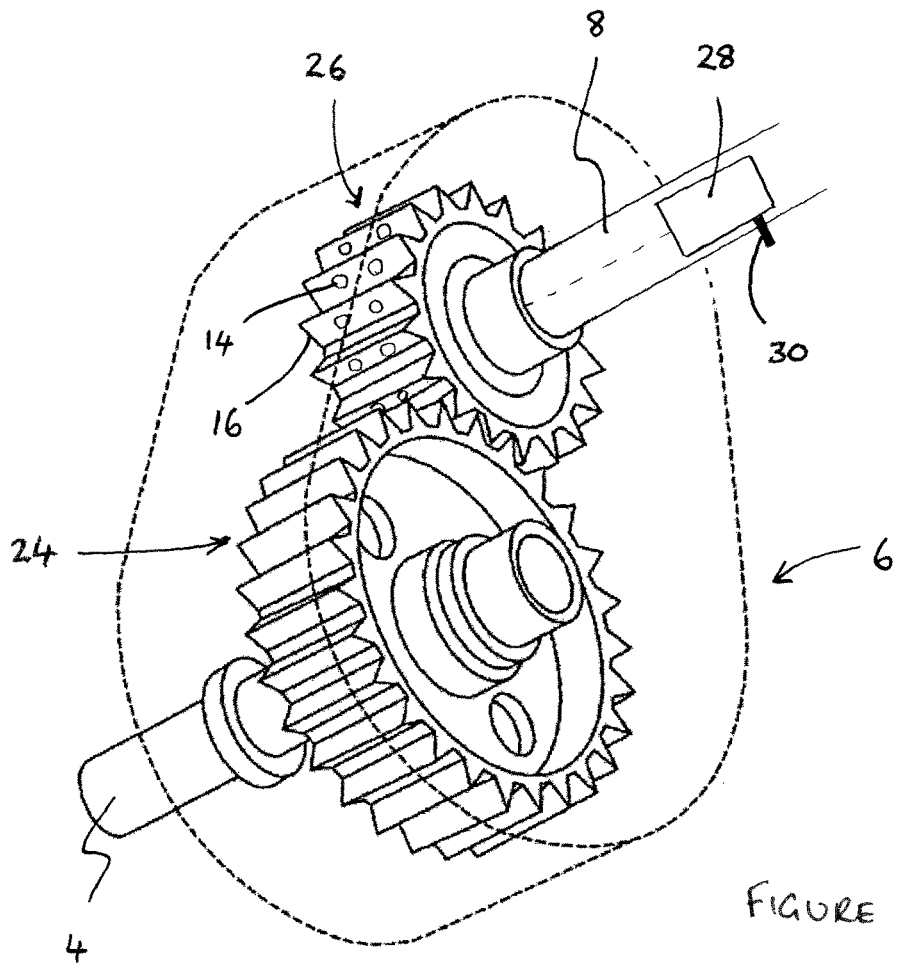
FIG. 8 is a schematic perspective diagram of a first monitoring gear arrangement in a gearbox, showing a data transfer telemetry system.
Figure 9:
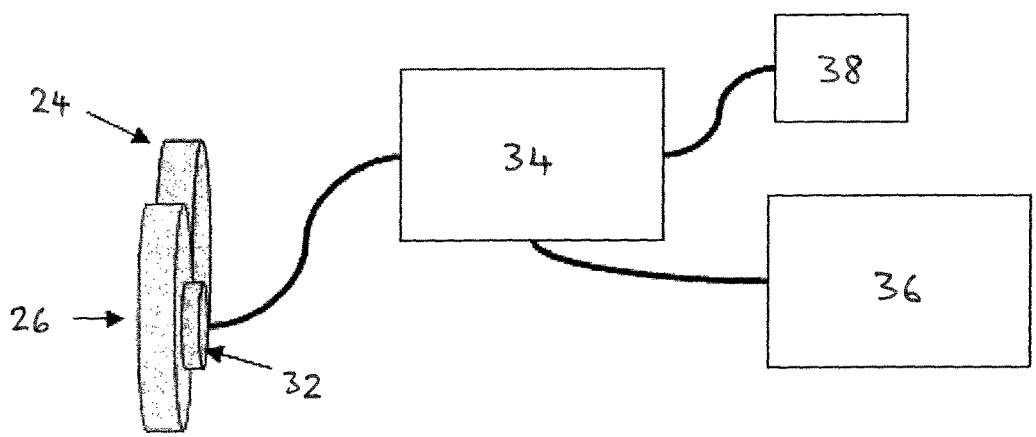
FIG. 9 is a system overview of a monitoring apparatus.

FIG. 8 is a schematic diagram of a gearbox 6 containing a driving gear 24 connected to a rotor shaft 4 and a follower gear 26 connected to an output shaft 8. In the illustrated arrangement the follower gear 26 is a monitoring gear for the driving gear 24. The follower gear 26 includes one or inductive sensors 14, which may be arrayed in various of the gear teeth 16, as is described above. The follower gear 26 includes an electronic signal unit 28 connected to the sensors 14 in the gear teeth 16 and integrated into the output shaft 8. The signal unit 28 may carry out signal processing and/or data transmission. An antenna 30 is provided for wireless data transfer. FIG. 9 shows the driving gear 24 and follower gear 26 carrying a slip ring 32 to transmit signals to/from a sensor driver 34 that is connected to a data storage/processor unit 36 and a power supply unit 38.

In an alternative embodiment, the driving gear 24 may be provided with one or more inductive sensors so as to act as a monitoring gear for the follower gear 26. In fact either or both of the gears 24, 26 may have a sensing capability, so that either one can monitor the other, or both gears can monitor each other. Such arrangements allow for self-monitoring of a gearbox without necessarily requiring dedicated monitoring means to be accommodated in the gearbox.

Figure 10:
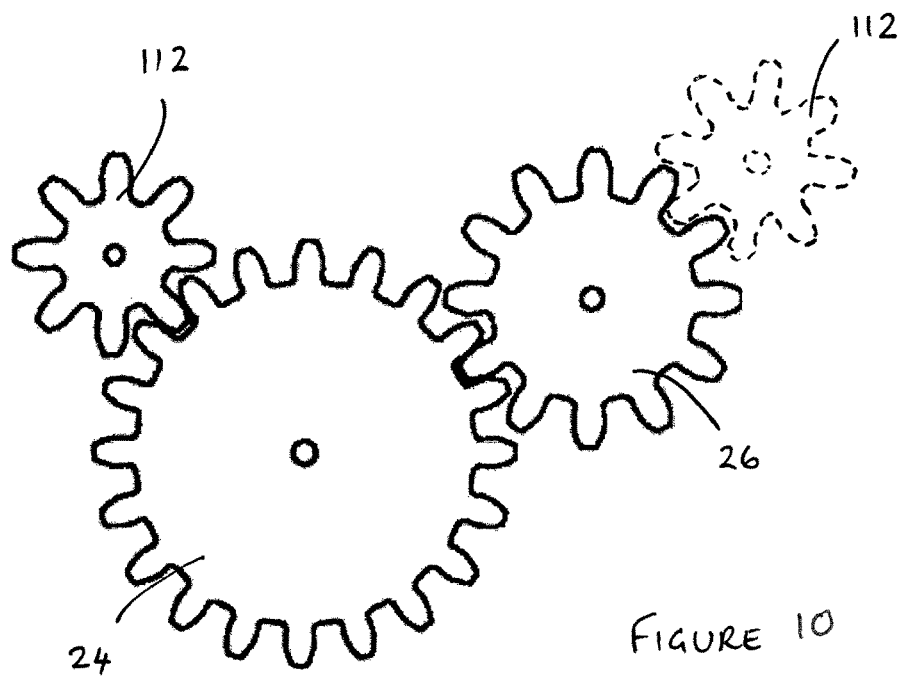
FIG. 10 is a partial schematic diagram of a second monitoring gear arrangement.

A potential drawback of integrating sensors with the working gears in a gearbox, i.e. those gears transmitting torque, is that the sensors may be exposed to forces that could interfere with their operation and/or integrity. FIG. 10 is a schematic diagram of a gear train comprising a driving gear 24 and a follower gear 26. In this system a dedicated monitoring gear 112 is provided to monitor the state of the driving gear 24. Another monitoring gear 112 (shown by a dotted outline) may optionally be provided for the follower gear 26. Here the monitoring gear(s) 112 are not transmitting force through the gearbox and are merely arranged to rotate freely, for example on a shaft mounted with bearings. As the teeth of the driving gear 24 and/or follower gear 26 mesh with those of a monitoring gear 112, one or more sensors mounted on or in the monitoring gear 112 scan the teeth of the working gears to detect surface flaws. The sensor signals can be used to issue an early warning when degradation is found to have reached a threshold level, so that preventative maintenance can be scheduled before gear failure occurs.

Figure 11:
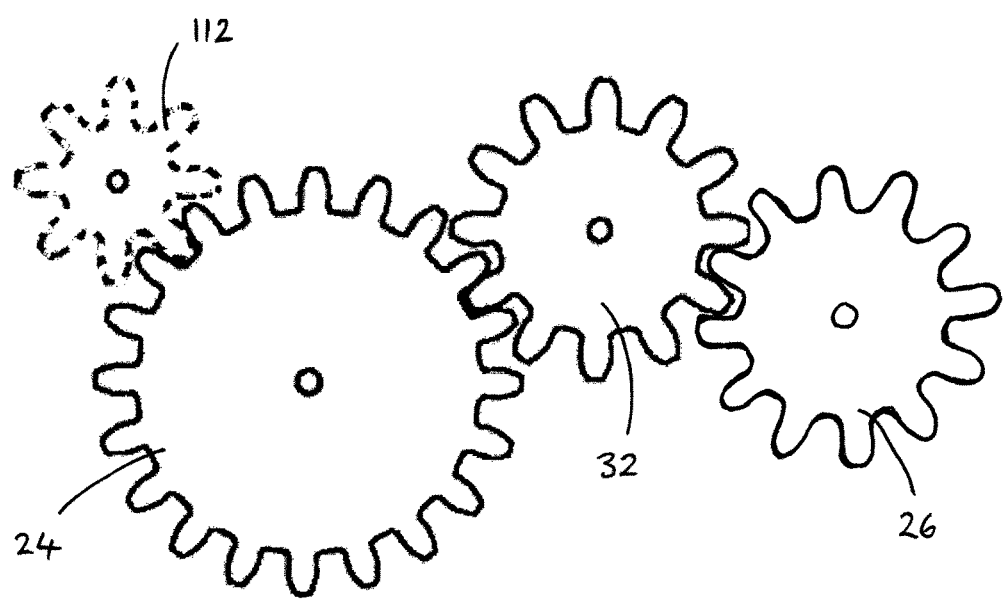
FIG. 11 is a partial schematic diagram of a third monitoring gear arrangement.

FIG. 11 depicts another gear train arrangement in which a driving gear 24 transmits the rotation of a main rotor shaft to a follower gear 26 via an idler gear 32. The idler gear 32 is an intermediate transmission gear which does not drive a shaft to perform any work but can be used to change the direction of rotation for the output shaft connected to the follower gear 26. For monitoring purposes the idler gear 32 can be provided with one or more sensors, like one of the monitoring gears 12, 12', 12" described above. The idler gear 32 can potentially be used to monitor both the driving gear 24 and the follower gear 26, with the different gear ratios being used to distinguish between the signals collected by the sensors as the teeth mesh at different rates. If it is not desirable to have to resolve two different monitoring signals from a single monitoring gear, the idler gear 32 could be used to monitor the follower gear 26 while another monitoring gear 112 (shown in dotted outline) is provided to monitor the driving gear 24. Of course, the arrangement could also be the other way round, with the idler gear 32 primarily monitoring the driving gear 24 and a separate monitoring gear (not shown) potentially provided for the follower gear 26.

Various arrangements may be contemplated for monitoring one or more gears in trains involving two, three or more gears. In planetary gear systems it will be readily understood that there may be space for a monitoring gear around the sun gear, to monitor the sun and/or planet gear(s). In any of these systems a mixture of working and/or non-working gears may be used for monitoring purposes.

While some preferred embodiments have been described in the context of toothed gears, it will be appreciated that the invention may find use in monitoring various types of gear, including worm gears and rack-and-pinions drives, as well as rotating engine components that may not have a toothed surface, such as belt drive wheels, engine shafts, clutch plates, etc. For example, instead of meshing gears, it can be envisaged that a rotating member carrying one or more inductive sensors may be mounted so as to scan the sensor(s) across the surface of a rotor shaft as they rotate relative to one another. The engine could take the form, for example, of an internal combustion engine, a gas turbine engine or any electricity-generating turbine, including wind and water turbines.

EXAMPLES

Example 1

Bench tests were carried out to assess the use of embedded eddy current sensors for gear monitoring and damage detection applications. A simplified gearbox test rig was built using two rotating shafts to mount a pair of mating 'spur' gears. A primary driving gear was fitted to the output shaft of a motor. A secondary monitoring gear was fitted to a driven shaft that fed into an electric motor which acted as a magnetic drag brake, to provide mechanical resistance to the driven shaft. Each shaft was fitted with precision optical shaft encoders, which provided 500 pulses and 1 pulse per revolution.

The primary gear was a steel gear wheel having 25 teeth. The secondary monitoring gear was a plastic gear wheel with 24 teeth, so as to permit a rolling scan of all 25 teeth of the primary gear over 25 revolutions. The secondary monitoring gear had ferrite-cored eddy current sensors embedded in the teeth. FIGS. 12a-12c shows the different eddy current sensors in different teeth. In FIGS. 12a and 12b, a 2 mm diameter cylindrical sensor is fitted. FIG. 12a shows a face sensor with the coil axis perpendicular to the tooth face. FIG. 12b shows a root sensor with the coil axis aligned with the tooth axis. In FIG. 12c it is proposed to fit an elongate sensor (e.g. of length 10-15 mm) in a face of the tooth. The monitoring gear was fitted with a selector switch enabling any of the coils to be connected to the sensor coupling ring.

To establish a baseline, a primary gear made of steel with no defects was monitored first. Various different primary gears were then mounted on the output shaft, each having a defect machined into at least one of the teeth or otherwise showing signs of damage. The seeded faults are shown in FIGS. 12d-12f below the sensors that were expected to detect them. FIG. 12d shows a single transverse groove across the mid-point of the tooth face, FIG. 12e shows a single transverse groove across the root of the tooth, and FIG. 12f shows a punch mark on one side of the tooth face. The output signals from the eddy current sensors of FIGS. 12a and 12b were measured and the results are shown in FIGS. 13a and 13b above the corresponding defects. The sensor design of FIG. 12c has not yet been tested on this rig but the predicted change in output signal is shown in FIG. 13c, based on data taken from the elongate sensor in a different test rig. The output signal A is for the undamaged tooth as compared to the output signal B for the tooth with a defect. It can be seen from FIGS. 13a-13c that the defects produce distinct shape changes in the output signal, which are sufficiently different from the baseline signal to be detected by signal processing algorithms.

The sensors provide a very good signal-to-noise ratio. The sensor design was optimised to have closest proximity at the position where the fault was present. The resultant signals from the scan are therefore always prominently positioned at the minima position (maximum sensing condition) of the system output. Of course defects at other positions may also be detected, but the purpose of this test was to optimise sensing conditions.

Example 2

In addition to the seeded faults detected in Example 1, there was also tested another gear that had previously been run on a gearbox test rig and had built up some galling damage on the gear teeth. A sensor mounted in a tooth face (as seen in FIG. 12a) was used to monitor the gear. FIG. 14 shows the signals from the sensor, with the output signal A for an undamaged gear and the output signal B for the galled gear. The upper plot shows the sensor signal for a group of teeth exhibiting signs of galling damage while the lower plot is a close-up view of the sensor signal from a single tooth. From the upper plot it can be seen that there is a reduction in amplitude for the galled gear relative to the healthy for all of the teeth shown. This is due to an increased separation between the sensor and the surface of the teeth as the faces are worn down by galling. From the lower plot it can be seen that the output signal has not only a reduction in amplitude but also a modified shape. This shows that the gear is not merely misaligned but there is a local reduction in the amount of material at the surface of the galled gear that results in the damaged surface sliding across the sensor with a greater mean separation.

Example 3

Figure 15:
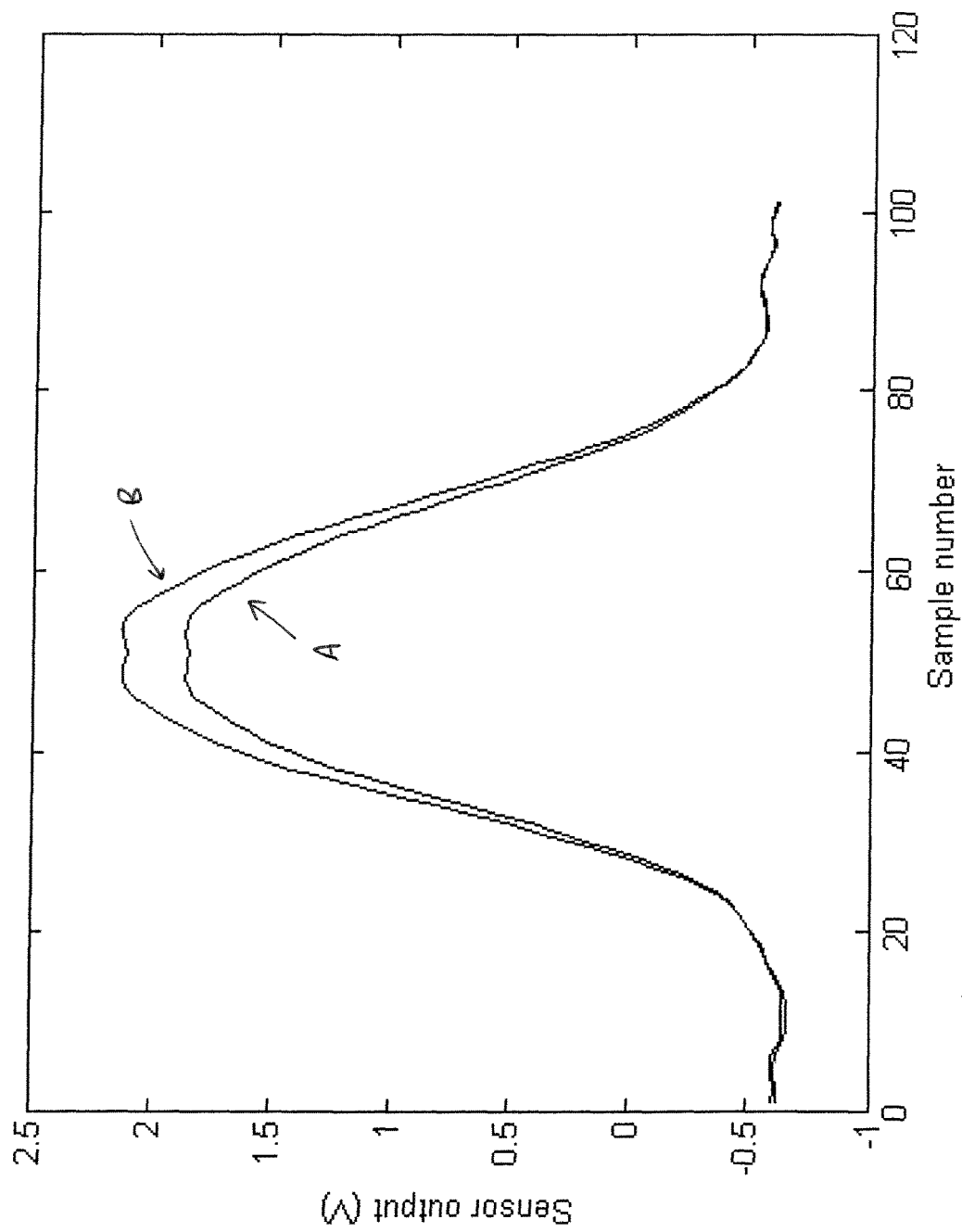
FIG. 15 shows the output signal from the eddy current sensor design of FIG. 12a when monitoring for gear misalignment.

By way of a comparative example, a misalignment test was run using the same gearbox test rig. The primary gear was run first in optimal alignment and then with a small radial offset (200 μm) applied by modifying the relative radial positioning of the gear wheels. The signal from the eddy current sensor mounted in a tooth face (as seen in FIG. 12a) was used to monitor the gear and the results are shown in FIG. 15. The output signal A is for the aligned gear as compared to the output signal B measured after misalignment. It can be seen that there is a bulk change in amplitude as the misalignment changes the separation between the teeth of the primary gear and the sensor. However there is no change in the shape of the output signal from the sensor. A misalignment problem can therefore be distinguished from local defects such a cracks or pits in a gear tooth.

The invention claimed is:

1. A method for monitoring local defects in one or more transmission gears of a gearbox during service, comprising:
arranging one or more eddy current sensor(s) to interact with the transmission gear(s) as they are rotating during service, wherein the one or more eddy current sensor(s) are carried by a monitoring gear or part of a monitoring gear that is shaped so as to enmesh with the transmission gear(s) to be monitored thereby to pass the sensor(s) across a portion of a surface of the transmission gear(s) during relative movement therebetween;
measuring an amplitude of an output signal from the eddy current sensor(s) resulting from interaction with the rotating engine component; and
detecting a change in shape of the amplitude of the output signal indicative of a local defect, wherein the detecting of the change in shape of the amplitude of the output signal comprises processing the output signal to distinguish the change in shape of the amplitude of the output signal from a bulk change in amplitude of the output signal which indicates a misalignment of the one or more transmission gears, thereby distinguishing the local defect from the misalignment of the one or more transmission gears.

2. The method of claim 1, further comprising:
detecting a bulk change in amplitude of the output signal.

3. The method of claim 1, further comprising:
measuring a datum output signal from the eddy current sensor(s) when the rotating engine component is initially installed; and
detecting at least one of a) a change in shape, and b) a change in shape and a bulk change in amplitude of the output signal by comparison to the datum output signal.

4. The method of claim 1, further comprising adjusting a frequency at which the eddy current sensor(s) are driven.

5. The method of claim 1, wherein the or each transmission gear to be monitored comprises a plurality of transmission gear teeth, and wherein at least one of a size, a shape and a position of the eddy current sensor(s) is selected so that the sensor(s) traverse across a surface of the transmission gear teeth as the monitoring gear or part thereof and the transmission gear(s) enmesh.

6. The method of claim 1, wherein the monitoring gear or part thereof comprises one or more monitoring gear teeth, and wherein the one or more eddy current sensor(s) are carried by the one or more monitoring gear teeth.

7. The method of claim 6, wherein at least one of the monitoring gear teeth is provided with the sensor(s), wherein the or each transmission gear to be monitored comprises a plurality of transmission gear teeth wherein a respective ratio between the number of monitoring gear teeth on the monitoring gear and the number of transmission gear teeth on the gear(s) being monitored is selected to ensure that every tooth of each monitored gear is tested after a number of revolutions.

8. The method of claim 1, wherein the eddy current sensor(s) comprise a respective ferrite core.

9. An apparatus for monitoring a gearbox, the apparatus comprising:
one or more transmission gears;
a monitoring gear or part of a monitoring gear carrying one or more eddy current sensor(s) arranged to interact with the transmission gear(s) to monitor local defects in the transmission gear(s) as they are rotating in the gearbox during service, wherein the monitoring gear or the part of the monitoring gear is shaped so as to enmesh with the transmission gear(s) to be monitored thereby to pass the sensor(s) across a portion of a surface of the transmission gear(s) during relative movement therebetween;
a device arranged to measure an amplitude of an output signal from the eddy current sensor(s) resulting from interaction with the transmission gear(s); and
a processor arranged to process the output signal to detect a change in shape of the amplitude of the output signal indicative of a local defect, wherein the detecting of the change in shape of the amplitude of the output signal indicative of the local defect comprises processing the output signal to distinguish the change in shape of the amplitude of the output signal indicative of a local defect from a bulk change in amplitude of the output signal which indicates a misalignment of the one or more transmission gears, thereby distinguishing the local defect from the misalignment of the transmission gear(s).

10. The apparatus of claim 9, wherein the processor is arranged to detect a bulk change in amplitude of the output signal.

11. The apparatus of claim 9, wherein the device is arranged to measure a datum output signal from the eddy current sensor(s) when the transmission gear(s) is/are initially installed; and
the processor is arranged to detect at least one of a) a change in shape, and b) a change in shape and a bulk change in amplitude of the output signal by comparison to the datum output signal.

12. The apparatus of claim 9, comprising a driver arranged to adjust a frequency at which the eddy current sensor(s) are driven.

13. The apparatus of claim 9, wherein a single eddy current sensor is carried by the monitoring gear or part of a monitoring gear.

14. The apparatus of claim 9, wherein the one or more eddy current sensor(s) comprise an array of a plurality of sensors.

15. The apparatus of claim 14, wherein the sensors in the array have one or more different orientations.

16. The apparatus of claim 9, wherein the one or more eddy current sensor(s) comprise a number of different sensors, the sensors differing in terms of at least one of size, shape and mounting position.

17. The apparatus of claim 9, wherein the one or more eddy current sensor(s) are mounted below a surface of the monitoring gear or part of a monitoring gear.

18. The apparatus of claim 9, wherein the one or more eddy current sensor(s) are integrated into the monitoring gear or part of a monitoring gear.

19. The apparatus of claim 9, wherein the monitoring gear or part thereof comprises one or more monitoring gear teeth, and wherein the one or more eddy current sensor(s) are carried by the one or more monitoring gear teeth.

20. The apparatus of claim 19, wherein at least one of the monitoring gear teeth is provided with the sensor(s), wherein the or each transmission gear to be monitored comprises a plurality of transmission gear teeth wherein a respective ratio between the number of monitoring gear teeth on the monitoring gear and the number of transmission gear teeth on the gear(s) being monitored is selected to ensure that every tooth of each monitored gear is tested after a number of revolutions.

21. The apparatus of claim 9, further comprising:
a wireless data transfer telemetry system configured to transfer signals from the one or more eddy current sensor(s).

22. The apparatus of claim 9, wherein the or each transmission gear to be monitored comprises a plurality of transmission gear teeth, and wherein at least one of a size, a shape and a position of the eddy current sensor(s) is selected so that the sensor(s) traverse across a surface of the transmission gear teeth as the moveable member and the transmission gear(s) enmesh.

23. The apparatus of claim 9, wherein the eddy current sensor(s) comprise a respective ferrite core.

* * * * *